US006486369B1

(12) United States Patent
Voight et al.

(10) Patent No.: US 6,486,369 B1
(45) Date of Patent: Nov. 26, 2002

(54) PROCESS FOR SELECTIVE HYDROGENATION OF AN OLEFINIC FEED STREAM CONTAINING ACETYLENIC AND DIOLEFINIC IMPURITIES

(75) Inventors: Richard W. Voight, Houston, TX (US); Steven A. Blankenship, Radcliffe, KY (US)

(73) Assignee: Sud-Chemie Inc., Louisville, KY (US)

( * ) Notice: Subject to any disclaimer, the term of this patent is extended or adjusted under 35 U.S.C. 154(b) by 0 days.

(21) Appl. No.: 09/691,542

(22) Filed: Oct. 18, 2000

(51) Int. Cl.[7] .................. C07C 7/163; C07C 7/167; C07C 5/03; C07C 5/09
(52) U.S. Cl. .................. 585/259; 585/258; 585/260; 585/261; 585/264
(58) Field of Search .................. 585/258, 254, 585/260, 261, 264

(56) References Cited

U.S. PATENT DOCUMENTS

| | | | | | |
|---|---|---|---|---|---|
| 3,113,980 | A | | 12/1963 | Robinson | 585/260 |
| 3,679,763 | A | * | 7/1972 | Livington | 585/262 |
| 4,126,645 | A | | 11/1978 | Collins | 585/260 |
| 4,329,530 | A | | 5/1982 | Irvine et al. | 585/254 |
| 4,347,392 | A | | 8/1982 | Cosyns et al. | 585/254 |
| 4,367,353 | A | | 1/1983 | Inglis | 585/258 |
| 5,414,170 | A | | 5/1995 | McCue et al. | 585/264 |
| 5,648,576 | A | | 7/1997 | Nguyen Than et al. | 585/260 |
| 5,866,735 | A | * | 2/1999 | Chueng et al. | 585/273 |
| 5,889,138 | A | | 3/1999 | Summers | 528/310 |
| 5,925,799 | A | | 7/1999 | Stanley et al. | 585/254 |

FOREIGN PATENT DOCUMENTS

GB 916056 1/1963

* cited by examiner

Primary Examiner—Thuan D. Dang
(74) Attorney, Agent, or Firm—Scott R. Cox

(57) ABSTRACT

A process for selective hydrogenation of a $C_2$ and $C_3$ olefinic feed stream containing acetylenic and diolefinic impurities whereby the acetylenes and diolefins impurities are selectively hydrogenated concurrently in a vapor phase process without first separating the $C_2$ and $C_3$ olefinic gases into separate feed stream.

14 Claims, 3 Drawing Sheets

FIG. 3

CATALYST: G-58B, lot 89-1, 3x6 mesh, 25cc
TEST: 100 hours

BY THE OLD PROCESS

C2 ONLY

| | WEIGHT CONVERTED (grams) |
|---|---|
| C2H2 | 145.05 |
| MA | 0 |
| PD | 0 |
| TOTAL CONVERTED | 145.05 |

| | WEIGHT FORMED (grams) |
|---|---|
| GREEN OIL | 0.8732 |
| HEAVY POLYMER | 3.6846 |
| C4'S | 33.6639 |
| C6'S | 11.1001 |
| TOTAL OLIGOMERS | 49.32 |

| | % WT FORMED/ WT CONV |
|---|---|
| GREEN OIL | 0.60% |
| HEAVY POLYMER | 2.54% |
| C4'S | 23.21% |
| C6'S | 7.65% |
| TOTAL OLIGOMERS | 34.00% |

C2 SELECTIVITY: 27.34%

C3 ONLY

| | WEIGHT CONVERTED (grams) |
|---|---|
| C2H2 | 0 |
| MA | 203.36 |
| PD | 57.12 |
| TOTAL CONVERTED | 260.48 |

| | WEIGHT FORMED (grams) |
|---|---|
| GREEN OIL | 0.1284 |
| HEAVY POLYMER | 0.5445 |
| C4'S | 0 |
| C6'S | 40.6850 |
| TOTAL OLIGOMERS | 41.36 |

| | % WT FORMED/ WT CONV |
|---|---|
| GREEN OIL | 0.05% |
| HEAVY POLYMER | 0.21% |
| C4'S | 0.00% |
| C6'S | 15.62% |
| TOTAL OLIGOMERS | 15.88% |

C3 SELECTIVITY: 26.13%

SUMATION OF OLD PROCESSES

| | % WT FORMED/ WT CONV |
|---|---|
| | 0.65% |
| | 2.75% |
| | 23.21% |
| | 23.27% |
| | 49.88% |

BY THE NEW PROCESS

C2+C3

| | WEIGHT CONVERTED (grams) |
|---|---|
| C2H2 | 84.23 |
| MA | 68.67 |
| PD | 17.49 |
| TOTAL CONVERTED | 170.38 |

| | WEIGHT FORMED (grams) |
|---|---|
| GREEN OIL | 1.0204 |
| HEAVY POLYMER | 4.2141 |
| C4'S | 12.066 |
| C6'S | 18.488 |
| TOTAL OLIGOMERS | 35.79 |

| | % WT FORMED/ WT CONV |
|---|---|
| GREEN OIL | 0.60% |
| HEAVY POLYMER | 2.47% |
| C4'S | 7.08% |
| C6'S | 10.85% |
| TOTAL OLIGOMERS | 21.00% |

C2 SELECTIVITY: 48.26%

C3 SELECTIVITY: 98.02%

PROCESS IMPROVEMENTS

58% REDUCTION OF FOULANT LEVELS

MUCH GREATER SELECTIVITIES

PROCESS FOR SELECTIVE HYDROGENATION OF AN OLEFINIC FEED STREAM CONTAINING ACETYLENIC AND DIOLEFINIC IMPURITIES

CROSS REFERENCE TO RELATED APPLICATIONS

NONE

BACKGROUND OF INVENTION

1. Field of Invention

This invention relates to a process for selective hydrogenation of an olefinic feed stream containing acetylenic and diolefinic impurities. More particularly, this invention relates to a process for selective hydrogenation of a $C_2$ and $C_3$ olefinic feed stream containing acetylenic and diolefinic impurities without first separating the $C_2$ olefins from the $C_3$ olefins, whereby the hydrogenation of the acetylenic and diolefinic impurities occurs in a single processing step. This invention also relates to a catalyst and to its use in this process for selective hydrogenation.

2. Prior Art

The manufacture of unsaturated hydrocarbons usually involves cracking various types of hydrocarbons and often produces a crude product containing hydrocarbon impurities that are more unsaturated than the desired product. These unsaturated hydrocarbon impurities are often very difficult to separate by fractionation from the desired product. The most common example is ethylene manufacture, in which acetylenes are common by-products. In a similar way, formation of propylene produces $C_3 H_4$ (methyl acetylene or allene) and butadiene. Further, it has often been difficult industrially to remove such undesirable, highly unsaturated hydrocarbons by hydrogenation so that no significant hydrogenation of desired hydrocarbon takes place. One example of this catalytic process is described in UK Pat. No. 916,056.

Two general types of gas phase selective hydrogenation processes for removing undesired, unsaturated hydrocarbons have come into use. One, known as "front-end" hydrogenation, involves passing the crude gas from the initial cracking step, after removal of steam and condensible organic material, over a hydrogenation catalyst. Despite the large hydrogen content of such gas, which is very greatly in excess of the acetylenes and sufficient to hydrogenate a substantial part of the olefin present, operation with sufficient selectivity to produce olefins of polymerization quality is well established and catalyst lives of many years are obtained. In the other type of gas phase selective hydrogenation, known as "tail-end" hydrogenation, the crude gas is fractionated and the resulting concentrated product streams are individually reacted with hydrogen in a slight excess over the quantity required for hydrogenation of the highly unsaturated hydrocarbons which are present. However, in tail-end use there is a greater tendency for deactivation of the catalyst, and consequently, periodic regeneration of the catalyst is necessary.

It has been proposed to employ both front-end and tail-end selective hydrogenation in the same plant.

Further, although the above-mentioned processes are normally carried out in the gaseous phase, it has also been proposed to perform these hydrogenation reactions with the hydrocarbon in a liquid phase, especially when the feed contains compounds containing four or more carbon atoms in the molecule.

A number of patents have discussed selective hydrogenation of such unsaturated hydrocarbons, including U.S. Pat. Nos. 4,126,645, 4,367,353, 4,329,530, 4,347,392 and 5,414,170.

Catalysts that have been found to be suitable for such selective hydrogenation reactions include palladium supported on an alumina substrate, as disclosed for example in U.S. Pat. Nos. 3,113,980, 4,126,645 and 4,329,530. The catalyst used for these reactions is normally formed as shaped pieces, such as pellets. The palladium on alumina catalysts generally have a surface area in the range of 5 to 200 $m^2/g$ and a pore volume of at least 0.4 $cm^3/g$, with the radii of the pores greater than 300 angstroms. The amount of the palladium present in the catalyst is generally in the range of about 0.1 to about 1 percent, as disclosed in U.S. Pat. No. 4,367,353 and from 0.01 to 5 percent, as disclosed in U.S. Pat. No. 3,113,980.

Other types of gas phase palladium on alumina catalysts for the selective hydrogenation of acetylene compounds are disclosed, for example, in U.S. Pat. Nos. 5,925,799, 5,889,138, 5,648,576 and 4,126,645.

Current tail-end, selective hydrogenation technology for $C_2$ and $C_3$ feeds employs two separate and distinct processing lines, one for the selective hydrogenation of $C_2$ olefin compounds and one for the selective hydrogenation of the $C_3$ olefin compounds. The $C_2$ compounds with their related contaminants are first separated from the $C_3$ compounds and their related contaminants. This separation results in the formation of two distinct feed streams. Each of these feed streams is then independently reacted with hydrogen and carbon monoxide in the presence of a palladium catalyst to selectively hydrogenate the respective $C_2$ and $C_3$ contaminants.

The current tail-end technology has several deficiencies including (1) higher production of heavy oligomers resulting in shorter operating cycles, (2) lower average selectivity, (3) the need for frequent regeneration, and (4) the need for the introduction of carbon monoxide to the process feed stream to improve catalyst selectivity. (The carbon monoxide must be subsequently removed from the feed stream in a further processing step.) In addition, (5) this two-stage process is more expensive to perform than would be a single-stage process, at least partially because of increased capital costs, and can result in the formation of certain longer chain by-products resulting in loss of the desired olefin end products.

Accordingly, it is an object of this invention to disclose a process for the selective hydrogenation of a $C_2$ and $C_3$ olefinic feed stream containing $C_2$ and $C_3$ acetylenic and diolefinic impurities.

It is a further object of the invention to disclose a process for the selective hydrogenation of a $C_2$ and $C_3$ olefinic feed streams containing $C_2$ and $C_3$ acetylenic and diolefinic impurities without first separating the $C_2$ olefins from the $C_3$ olefins, thereby utilizing a single process step, whereby $C_2$ and $C_3$ acetylenic and diolefinic impurities are removed in a single process step.

It is a still further object of this invention to disclose a catalyst useful for the single-stage, selective hydrogenation of a $C_2$ and $C_3$ olefinic feed stream containing $C_2$ and $C_3$ acetylenic and diolefinic impurities in a single process step.

It is a still further object of this invention to disclose process steps for a single-stage selective hydrogenation of a $C_2$ and $C_3$ olefinic feed stream containing $C_2$ and $C_3$ acetylenic and diolefinic impurities, whereby the quantity of the desirable $C_2$ and $C_3$ olefins is not substantially reduced.

It is a still further object of this invention to disclose the process conditions for a single-stage hydrogenation of a $C_2$ and $C_3$ olefinic feed stream containing $C_2$ and $C_3$ acetylenic and diolefinic impurities.

These and other objects can be obtained by the disclosed process for the selective hydrogenation of a $C_2$ and $C_3$ olefinic feed stream containing $C_2$ and $C_3$ acetylenic and diolefinic impurities which is disclosed by the present invention.

SUMMARY OF THE INVENTION

The present invention is a process for the single-stage selective hydrogenation of a $C_2$ and $C_3$ olefinic feed stream containing acetylenic and diolefinic impurities comprising preparing a $C_2$ and $C_3$ olefinic feed stream, which stream may include acetylenes, diolefins and certain low molecular weight, light-end gases selected from the group consisting of hydrogen, carbon monoxide and methane;

separating from the feed stream the light end gases to generate a $C_2$ and $C_3$ olefinic feed stream which includes $C_2$ and $C_3$ acetylene and diolefin impurities; hydrogenating the $C_2$ and $C_3$ acetylene and diolefin impurities in a single feed stream over a catalyst bed by the addition of hydrogen to the feed stream to yield a $C_2$ and $C_3$ olefinic feed stream with substantially reduced quantities of $C_2$ and $C_3$ acetylene and diolefinic impurities while not substantially reducing the quantities of the $C_2$ and $C_3$ olefins in the feed stream; and separating the $C_2$ olefins from the $C_3$ olefins.

In a preferred embodiment of the process for the single-stage selective hydrogenation of a $C_2$ and $C_3$ olefinic feed stream containing $C_2$ and $C_3$ acetylenic and diolefinic impurities as discussed above, the feed stream comprises from about 15 to about 50 percent by weight ethylene, from about 10 to about 25 percent by weight ethane, from about 25 to about 50 percent by weight propylene and from about 10 to about 25 percent by weight propane.

In a further preferred embodiment, the single-stage selective hydrogenation process as discussed above is utilized in a "tail-end" selective hydrogenation unit.

In another preferred embodiment the catalyst useful for the process for the single-stage, selective hydrogenation of a $C_2$ and $C_3$ olefinic feed stream containing $C_2$ and $C_3$ acetylenic and diolefinic impurities comprises a palladium on alumina catalyst.

BRIEF DESCRIPTION OF THE DRAWINGS

FIG. 3 is a table showing a comparison of test performance between the old process shown in FIG. 1 and the process of the invention shown in FIG. 2.

DETAILED DESCRIPTION OF THE DRAWINGS

Figure 1:
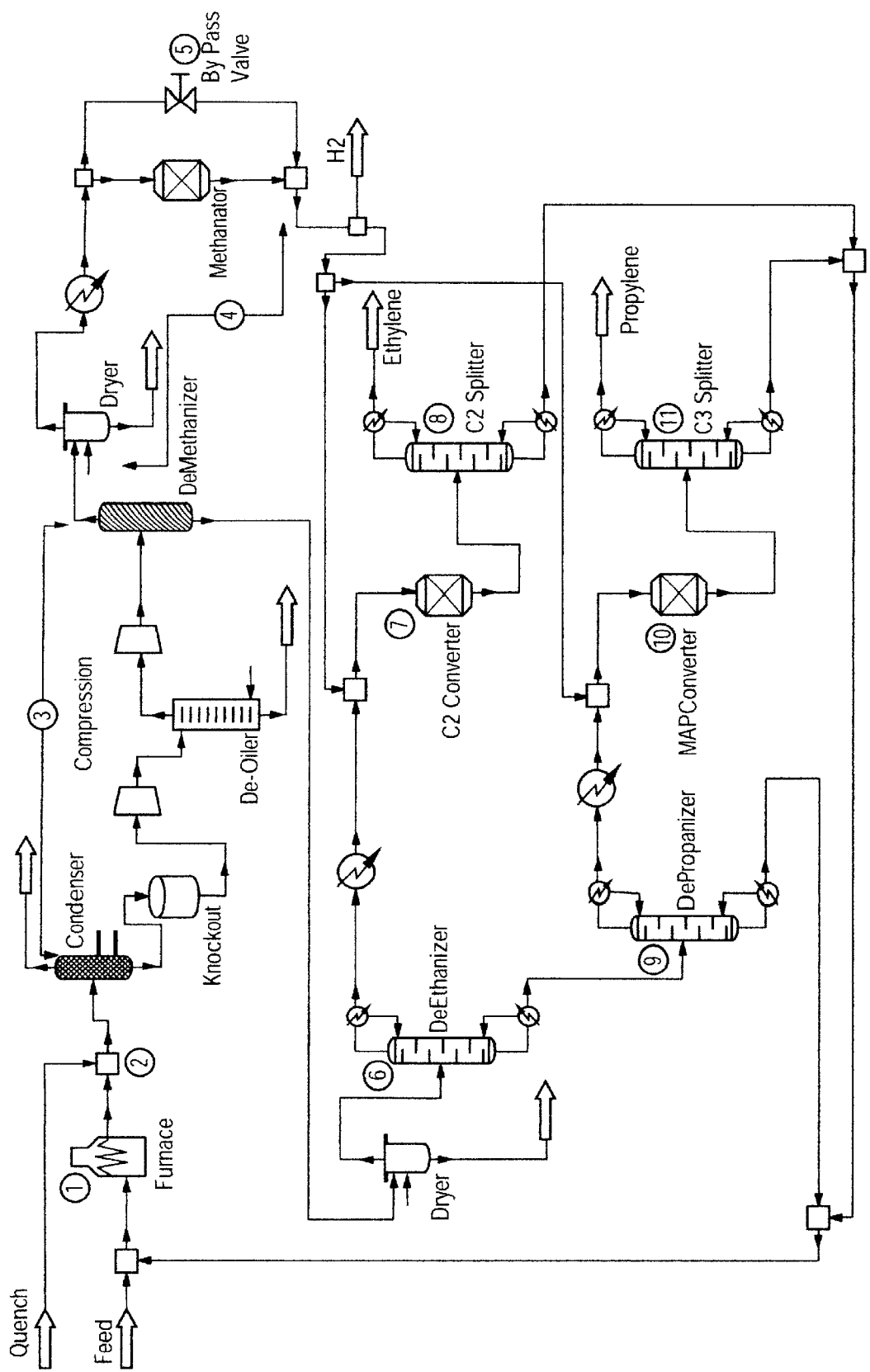
FIG. 1 is a diagram showing the prior art two-stage process used for the selective hydrogenation of a $C_2$ and $C_3$ olefinic feed stream containing $C_2$ and $C_3$ acetylenic and diolefinic impurities.
Figure 2:
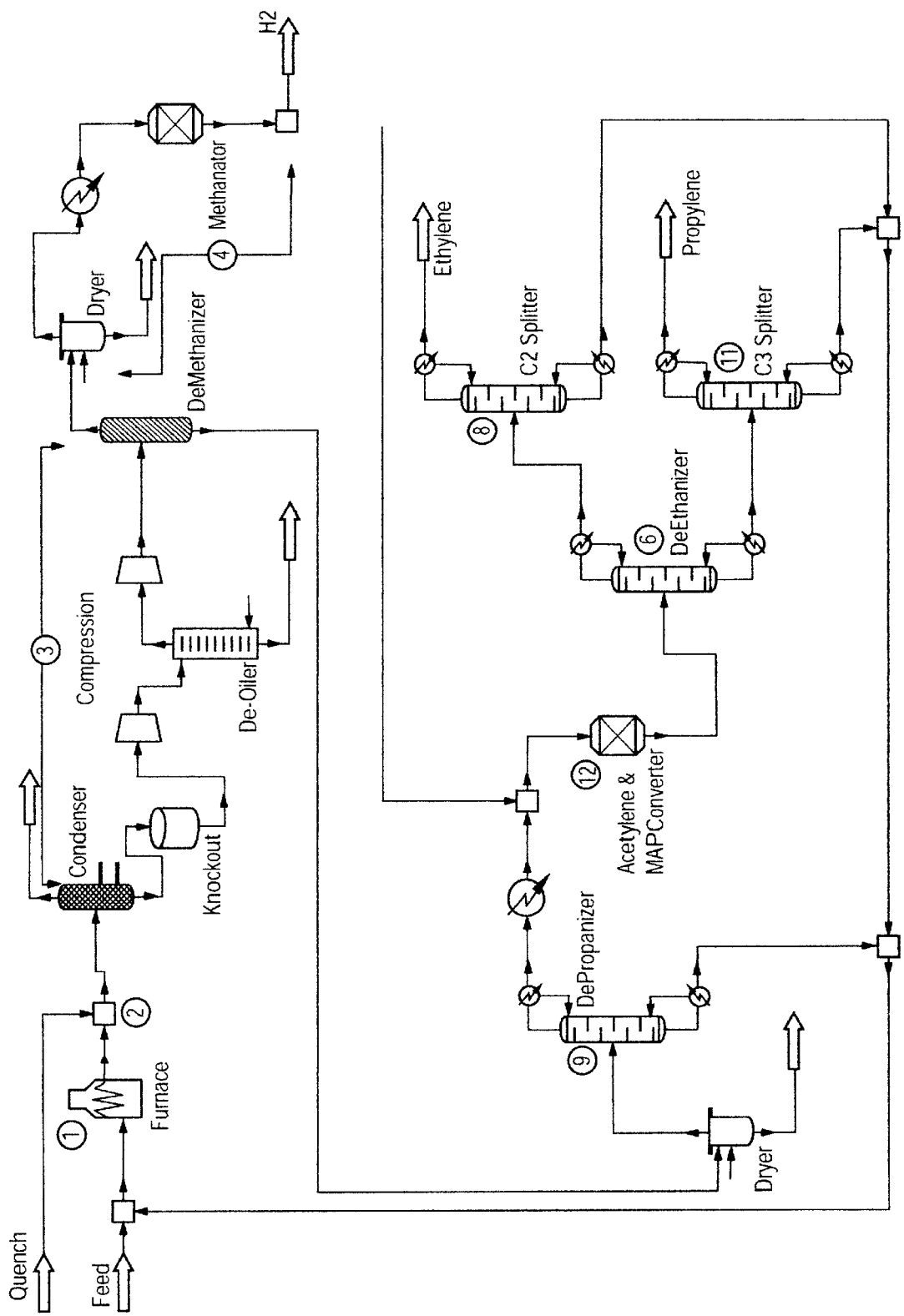
FIG. 2 is a diagram showing the process of the invention for a single-stage selective hydrogenation of $C_2$ and $C_3$ olefinic feed streams containing $C_2$ and $C_3$ acetylenic and diolefinic impurities.

The differences between the prior art process (FIG. 1) and the process of the invention (FIG. 2) are apparent from a comparison of the processes as disclosed in FIG. 1 and FIG. 2. The number designations on the separate Figures disclose the steps of the two respective processes. Each of the processes are "tail end" processes. While the process of the invention may be used with a front end or tail end process, preferably the process is used in a tail end process. The differences between the prior art process and the process of the invention are disclosed in the following description.

In the prior art process as shown in FIG. 1, the feed leaves the furnace (1) after cracking and goes through a quench drum (2) to rapidly cool down the gas. This is to prevent further cracking and resultant coke formation. This step is exactly the same in the new process of FIG. 2. The gas then passes through a heavy oil knockout stage and de-watering stage and then goes into a demethanizer. This stage in the process is identical in both the old and new processes (FIGS. 1 and 2).

The new process (FIG. 2) starts to differentiate itself from the old process (FIG. 1) in the hydrogen recovery step (4). The deMethanizer overhead feed consists of methane, hydrogen, carbon monoxide, and carbon dioxide. Sufficient hydrogen is present in both the new process and the old process to hydrogenate any of the acetylenes and diolefins that are present in this feed stream. Preferably the amount of hydrogen present is greater than the stoichiometric amount which is necessary to hydrogenate all acetylenes and diolefins present in the feed stream. Preferably, the amount of hydrogen present in the feed is from about 100 percent of the stoichiometric amount necessary for hydrogenation of all acetylenes and diolefins to about 150 percent of the stoichiometric amount.

This gas stream is sent to a cryogenic drying section followed by CO and $CO_2$ conversion to $CH_4$ and $H_2O$ in a methanator or PSA unit. The old process requires a bypass valve (5) around the methanator in order to supply CO as a selectivity enhancer for the hydrogen in the C2 converter and MAPD converter. The new process requires CO addition at this point in the flow scheme to the combination C2/C3 reactor. Water formed is removed in a mole sieve bed. The dried and purified hydrogen is added to the hydrogenation reactors of both the old and new processes.

In the old process (FIG. 1) the deMethanizer bottom feed, containing C2 and heavier compounds, is sent to a deEthanizer (6). The C2 overhead feed contains C2 compounds primarily consisting of C2H4, C2H6 and trace levels of C2H2. The trace levels of C2H2 are removed by selective hydrogenation in a C2 converter (7). However, some ethane is produced from overhydrogenation of the acetylene which can be reduced with the addition of CO on ppm levels. Heavier oligomers are formed as a byproduct of the hydrogenation process. The ethane is separated from the ethylene in the C2 Splitter (8). Ethylene goes overhead and ethane exits in the bottom feed, which is recycled for cracking (1). Any oligomers formed are recycled to the cracker. The ethylene must be processed further to remove trace CO levels that are not desired in the polymerization process. The deEthanizer bottom feed containing C3 and heavier compounds is sent to a depropanizer tower (9) for separation. The dePropanizer overhead feed contains C3 compounds primarily consisting of C3H4, C3H8 and trace levels of MAPD (methyl acetylene and propadiene). The trace levels of MAPD are removed by selective hydrogenation in a separate C3 converter (10). Heavier oligomers are also formed during this hydrogenation process. Like in the C2 converter, overhydrogenation occurs and CO addition is required to minimize such process from occurring. The propylene is separated from the propane in a C3 splitter (11). The C3 splitter overhead contains propylene and propane which exits from the C3 splitter as a bottom feed for recycling to the cracker (1). Any oligomers formed also leave the C3 splitter in the bottom feed for recycling to the cracker (1). In a similar fashion CO is removed from the propylene feed for the down stream polymerization process.

In the new process the deMethanizer bottom feed, containing C2 and heavier compounds are sent to a dePropanizer (9). The dePropanizer overhead feed, containing C2H4, C2H6, trace acetylene, C3H6 and trace MAPD, is sent to a single selective hydrogenation converter (12). The hydrogenated feed stream is then sent to a deEthanizer (6) for further separation. The deEthanizer overhead feed consists of the C2H4 and C2H6 and is sent to a C2 splitter (8) for separation of the C2s. The C2 splitter overhead feed provides ethylene suitable for polymerization which does not contain CO. The C2 splitter bottom feed consists of C2H6 which is recycled to the cracking furnace (1). The deEthanizer bottom feed contains C3H6, C3H8 and any oligomers that are formed. This stream is fed to a C3 splitter (11) for further separation. The C3 splitter overhead feed consists of C3H6 suitable for polymerization which does not contain CO. The C3 splitter bottom feed contains C3H8 and any formed oligomers for recycle to the cracking furnace (1).

The feed stream at the beginning of the process is conventional and in one embodiment includes from about 15 to about 50 percent ethylene, 10 to about 25 percent ethane, 25 to 50 percent propylene and 10 to 25 percent propane plus C2 and C3 impurities. The feed streams may further include from 5 to 25 percent methane. It often includes acetylenic and diolefinic impurities from about 1.5 to about 3.0 percent by weight.

The catalyst that is used within the new process is preferably a palladium promoted catalyst, more preferably a palladium on alumina catalyst, such as G58C produced by Süd-Chemie Inc. The catalyst is preferably used in a multiple catalyst bed stream comprising from one to three separate catalyst beds, preferably three such beds.

The advantages of the new design include:

(1) Higher selectivity over the old design, at least about 10 percent and preferably at least about 20 percent higher;
(2) Lower capital costs because of the use of only one reactor instead of two;
(3) Substantial decrease of total oligomer formed resulting in higher olefin yield. This decrease is at least about 10 percent and preferably 25 percent or more.
(4) Substantial acetylene removal to a level of less than about 1 ppm.
(5) Substantial diolefin removal to a level of less than 1 ppm. and preferably where the total acetylenes and diolefins are reduced to a level of about 1 ppm.
(6) Reduction in the use of the amount of carbon monoxide to a level of less than about 10 ppm., preferably 1 ppm. to 3 ppm. in the olefinic feed stream prior to hydrogenation.

EXAMPLE 1

In order to test the process of the invention, the above process system of the invention as detailed in FIG. 2 was utilized in a bench scale fixed bed reactor. The feed stream containing the composition as detailed was introduced into a three bed catalyst system. The catalyst used was a G-58C catalyst supplied by Süd-Chemie, Inc. The conditions of the feed stream were 5,000 GHSV at 300 psig. The composition of the gas at the inlet and outlet at each stage in the processing is detailed below. Each of the systems was evaluated for 100 hours. The results for the new process are shown below:

| Gas Comp. | Bed # | | | | | |
|---|---|---|---|---|---|---|
| | 1 | | 2 | | 3 | |
| Mole. % | Inlet | Outlet | Inlet | Outlet | Inlet | Outlet |
| H2 | 2.22 | 0.01 | 0.13 | 0.003 | 0.04 | 0 |
| CH4 | 12.6 | 12.6 | 12.6 | 12.6 | 12.6 | 12.6 |
| C2H6 | 0.23 | 0.83 | 0.83 | 0.87 | 0.87 | 0.98 |
| C2H4 | 68.4 | 70.7 | 70.7 | 70.8 | 70.8 | 70.7 |
| C3H8 | 0.055 | 0.072 | 0.072 | 0.072 | 0.072 | 0.072 |
| C3H6 | 14.3 | 15.6 | 15.6 | 15.7 | 15.7 | 15.7 |
| C2H2 | 1.01 | 0.095 | 0.095 | <.0001 | <.0001 | <.0001 |
| Propadiene | 0.241 | 0.021 | 0.021 | 0.0043 | 0.0043 | <.0001 |
| Methyl Acetylene | 1.00 | 0.014 | 0.014 | 0.0024 | 0.0024 | <.0001 |
| H2:C2H2 & MAPD | 1:1 | | 1:1 | | 6:1 | |
| % C2H4 Gain/(Loss) | 0.31 | | 0.055 | | (0.115) | |
| % C3H6 Gain/(Loss) | 1.06 | | 0.091 | | 0.022 | |

As is shown the process of the invention successfully removed acetylene and MAPD to less than one part per million without the addition of carbon monoxide while providing an overall gain in the composition of ethylene and propylene. The first two beds operated at hydrogen levels slightly above the stochiometric amount needed to maximize selectivity, in the range of 1:1 to 1.5:1. The final bed required a higher percentage of hydrogen in the range of 4:1 to 6:1 to remove completely the propadiene. As a result there was a slight loss in ethylene.

EXAMPLE 2

G-58B, as supplied by Süd-Chemie Inc., was tested in a bench scale fixed bed reactor under the old process and the new process scheme. A comparison of the results of the old process and the new process is shown on FIG. 3.

No CO was supplied to the catalyst during the test period. Selectivity was clearly higher in the new process. The $C_2$ and $C_3$ old process selectivities were 27% and 26% respectively compared to 48% for $C_2$s and 98% for $C_3$s in the new process.

Oligomer formation was also reduced in the new process. The new process formed 21% total oligomers compared to 50% for the combined $C_2$ and $C_3$ process.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A process for the generation of separate streams of $C_2$ olefins and $C_3$ olefins with substantially reduced acetylene and diolefins from an olefinic feed stream containing acetylenic and diolefinic impurities comprising preparing a $C_2$ and $C_3$ olefinic feed which comprises $C_2$ and $C_3$ olefins, acetylenes, diolefins and light-end gases, wherein light-end gases comprise hydrogen, carbon monoxide, and methane, separating the light-end gases from the olefinic feed to generate an olefinic feed stream comprising $C_2$ and $C_3$ olefins, acetylenes and diolefins, without separating the $C_2$ and $C_3$ olefins into a separate $C_2$ feed stream and a separate $C_3$ feed stream, in a tail-end hydrogenation process substantially hydrogenating the acetylenes and diolefins impurities over a catalyst bed system containing a catalyst by the use of hydrogen to the feed stream to yield an olefinic stream with a substantially reduced quantity of acetylenes and diolefins impurities, and after hydrogenating the acetylenes and diolefins separating the $C_2$ olefins from the $C_3$ olefins.

2. The process of claim 1 wherein the amount of hydrogen present in the feed after separating the light-end gases and prior to hydrogenation is greater than a stoichiometric amount which is necessary to hydrogenate the acetylenes and diolefins present in the feed.

3. The process of claim 2 wherein the amount of the hydrogen present in the feed is from about 100 percent of the stoichiometric amount necessary for hydrogenation of the acetylenes and diolefins to about 150 percent of the stoichiometric amount.

4. The process of claim 1 wherein the catalyst bed comprises a multiple catalyst bed system comprising from one to three separate catalyst beds.

5. The process of claim 1 wherein the catalyst is a palladium-promoted catalyst.

6. The process of claim 5 wherein the palladium is placed on an alumina support.

7. The process of claim 1 wherein the composition of the feed stream after removal of light-end gases comprises from about 15 to about 50 percent by weight ethylene, from about 10 to about 25 percent by weight ethane, from about 25 to about 50 percent by weight propylene and from about 10 to about 25 percent propane.

8. The process of claim 7 wherein the feed stream further comprises from about 5 to about 25 percent methane.

9. The process of claim 1 wherein the amount of acetylenic and diolefinic impurities present in the feed stream after separating the light-end gases and prior to hydrogenation is from about 1.5 to about 3.0 percent by weight of the feed stream.

10. The process of claim 9 wherein the acetylenes are reduced to a level of less than about 1 ppm.

11. The process of claim 9 wherein the diolefins are reduced to a level of less than about 1 ppm.

12. The process of claim 9 wherein the acetylenes and diolefins after hydrogenation are reduced to a level to less than about 1 ppm.

13. The process of claim 1 wherein the amount of carbon monoxide in the olefinic feed stream after separating the light-end gases and prior to hydrogenation is less than about 10 ppm.

14. The process of claim 1 wherein the amount of carbon monoxide in the olefinic feed stream after separating the light-end gases and prior to hydrogenation is from about 1 ppm to about 3.0 ppm.

* * * * *